United States Patent [19]

Pagani

[11] Patent Number: 5,573,735
[45] Date of Patent: Nov. 12, 1996

[54] METHOD OF RETROFITTING UREA PRODUCTION PLANT

[75] Inventor: Giorgio Pagani, Milan, Italy

[73] Assignee: Urea Casale, S.A., Lugano, Switzerland

[21] Appl. No.: 478,693

[22] Filed: Jun. 7, 1995

Related U.S. Application Data

[62] Division of Ser. No. 354,482, Dec. 12, 1994, which is a division of Ser. No. 41,944, Apr. 2, 1993, Pat. No. 5,403,956.

[51] Int. Cl.$^6$ .............................. B01J 8/04; C07C 273/04
[52] U.S. Cl. ............................................ 422/189; 564/67
[58] Field of Search ...................................... 422/188, 189, 422/196, 234; 564/66, 67, 70, 72

[56] References Cited

U.S. PATENT DOCUMENTS

| | | | |
|---|---|---|---|
| 1,942,120 | 1/1934 | Plummer | 422/196 X |
| 3,049,563 | 8/1962 | Bochinski et al. | 564/70 |
| 3,091,637 | 5/1963 | Cook et al. | 564/72 |
| 3,222,040 | 12/1965 | Eckert | 261/94 |
| 4,094,903 | 6/1978 | Mavrovic | 564/66 |
| 4,354,040 | 10/1982 | Inoue et al. | 564/67 |
| 4,670,588 | 6/1988 | Zardi | 564/72 |
| 4,929,399 | 5/1990 | Lockett et al. | 261/112.2 |
| 5,276,183 | 1/1994 | Pagani et al. | 564/67 |
| 5,359,140 | 10/1994 | Granelli et al. | 564/67 |
| 5,380,943 | 1/1995 | Pagani et al. | 564/67 |

FOREIGN PATENT DOCUMENTS

| | | |
|---|---|---|
| 0479103 | 4/1992 | European Pat. Off. . |
| 1573707 | 4/1969 | France . |
| 1643092 | 3/1971 | Germany . |

OTHER PUBLICATIONS

U. Zardi, "Urea plants for tomorrow's world," *Nitrogen*, No. 135, Jan./Feb. 1982, pp. 26–37.

*Primary Examiner*—Robert Warden
*Assistant Examiner*—Christopher Y. Kim
*Attorney, Agent, or Firm*—Ostrolenk, Faber, Gerb & Soffen, LLP

[57] ABSTRACT

A process is described for the industrial synthesis of urea, making the ammonia ($NH_3$) and the carbon dioxide ($CO_2$) react, in at least on reaction space, at high pressures and temperatures and recycling at least in part the unreacted products obtained in a recycle section, characterized by: a) a synthesis reaction between reactants of high purity; and b) a synthesis reaction between less pure reactants, substantially recycled by the so-called recycle section. The corresponding new plant includes a rector (R1) of high yield ("once through"), a reactor (R2) of lower yield and a section of recovery and recycle. The application of the process to preexisting plants requires the simple addition of a reactor of high yield and of pumping device.

3 Claims, 3 Drawing Sheets

METHOD OF RETROFITTING UREA PRODUCTION PLANT

This is a division of application Ser. No. 08/354,482, filed Dec. 12, 1994, which is a division of 08/041,944, filed Apr. 2, 1993, now U.S. Pat. No. 5,403,956.

BACKGROUND OF THE INVENTION

The present invention concerns a process for the industrial synthesis of urea, making ammonia and carbon dioxide react in at least one reaction space, at high pressure and temperature, and recycling at least partially the unreacted products.

The invention concerns also the applications of this process to conventional systems in order to improve the urea yield and reduce energy consumptions.

New or modified plants obtained by the implementations of the above mentioned process and its applications to pre-existing systems, are within the scope of the invention.

Known are several types of processes, systems and plants for the industrial synthesis of urea from NH3 (in excess) and CO2, with recycling after stripping.

In order to have immediately clear ideas referring to emblematic cases, one among the most stated processes is the one based on the technology (Snamprogetti) of isobaric stripping with the synthesis reactor (stripping with NH3, selfstripping), (FIG. 1).

In the stripper (S) a great part of the carbamate included in the urea solution coming out of the reactor (R) and part of the free NH3 present are stripped and recycled into the reactor, whilst a urea solution (SU) coming from the stripper (S) having a relatively low content of residual CO2 (5÷7% weight) and obtaining a relatively high content of NH3 (22÷25% weight). This solution (SU) is treated in a middle pressure phase (SMP) where is it distilled at 18÷20 bar and the obtained vapours are sent to a rectification column (CR) enabling to obtain, first, NH3 at high purity (NEP) and then carbamate solution (SC).

The NH3 at high purity, after condensation, joins the NH3 feed (NA) and is pumped (pump P) into the reactor (R), and the same thing happens with the carbamate solution (pump P').

The main technical characteristics of the isobaric stripping process (Snamprogetti) can be resumed as follows:

synthesis pressure: approx. 150 bar

NH3/CO2 mol in the reactor: approx. 3.2÷3.4

H2O/CO2 mol in the reactor: approx. 0.6÷0.7 temperature of the reactor: 190° C.

yield: approx. 62÷63% vapour consumption: approx. 900 kg/MT urea

The above indicated values are rather consolidated and drastic improvements of the process do not seem to be possible.

Among the other processes with separate recycle of NH3 widely used in the past can be mentioned the ones of Toyo Engineering Ltd. indicated with the abbreviation TRC - TRC-I (Total Recycle C, TRC Improved), characterized by the fact that the ratio NH3/CO2 in the reactor is equal to approx. 4÷4.5 mol and the separation of NH3 at 18÷20 bar is more impressive than the previous process (Snamprogetti), also for the lack of a isobaric stripping.

Another generation of processes has been recently developed for increasing the yield in the reactor of the so called stripping processes (Snamprogetti NH3 selfstripping and Stamicarbon CO2 stripping), of the conventional values 55÷65% up to 70÷75%, providing at the same time, the above mentioned high yield reactors with isobaric loops.

Reference is made to the new and more recent processes as "IDR" (Isobaric Double Recycle) of Montedison and "ACES" of Toyo Engineering Ltd.

In the above mentioned recent processed "IDR" and "ACES", still operating with high ratios NH3/CO2 in the high yield reactor, all the unaltered reactants, including the high excess of NH3, are recycled to the reactor under the form of carbamate solution (the separate recycling of NH3 does not exist).

Without doubt much better yields are obtained (compared with the very first processes), but these advantages are coupled with a high complexity and complications in the construction of the equipment.

Furthermore these processes have the inconvenience of having to strip the unreacted products under high temperature conditions with real risks of decomposition of the (laboriously) developed urea.

OBJECT OF THE INVENTION

The first aim of the present invention is to provide a process without the above mentioned inconveniences, which can be operated easily, with total high yields and low consumptions.

Another aim of the invention is the applicability of this process to the conventional systems already having recycling sections for ammonia (or adapted with a new recycling section of the ammonia), reaching global yields of urea transformation in the synthesis sections equal or higher to the ones obtained with the modern processes "IDR", "ACES", etc.

A further aim of the invention is represented by the simple and effective plants (new or modified) resulting from the implementation of the said process.

SUMMARY OF THE INVENTION

These and other aims are obtained with the process according to the invention characterized by the fact that we have: a) a synthesis reaction between reactants of high purity; and b) a synthesis reaction between less pure reactants, substantially recycled by a recovery section.

The application of this process to conventional systems with recycling of ammonia is characterized by the simple addition of one high yield reactor as well as the devices for the additional pumping of reactants at the operative conditions of synthesis a).

The plant for the implementation (particularly ex-novo) of the process according to the invention is characterized at least by a first reactor (R1) of high yield (HY) fed with fresh CO2 and NH3 from the outside and with NH3 of high purity from recovery; a second reactor (R2) in parallel with the first one (R1) of yield lower than the first one and fed substantially with reactants from the recovery mixture; and a system of recovery section of the reactants from the reaction mixtures obtained from the first and second reactors.

DESCRIPTION OF THE PREFERRED EMBODIMENTS

Figure 1:
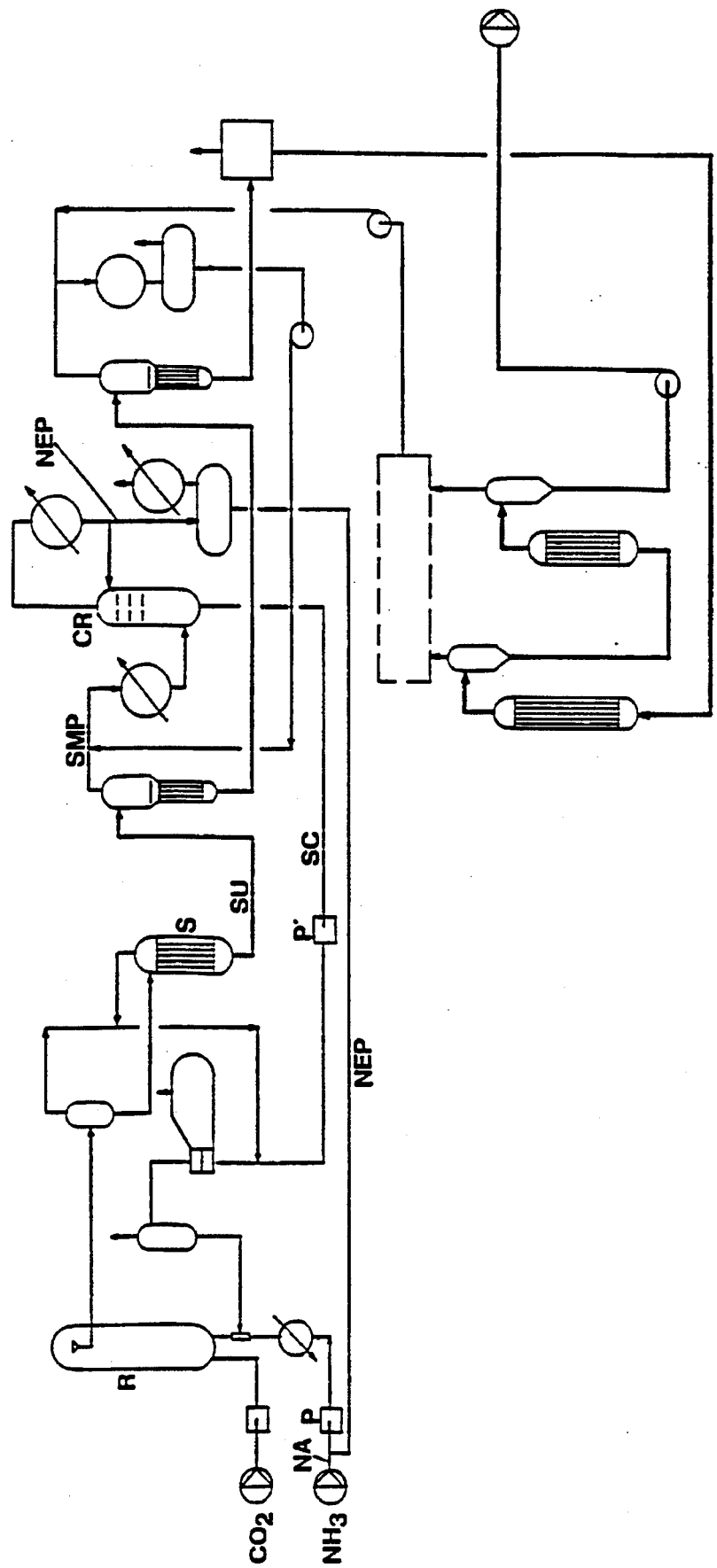
FIG. 1 is a diagrammatic representation of the prior art Snamprogetti process.
Figure 2:
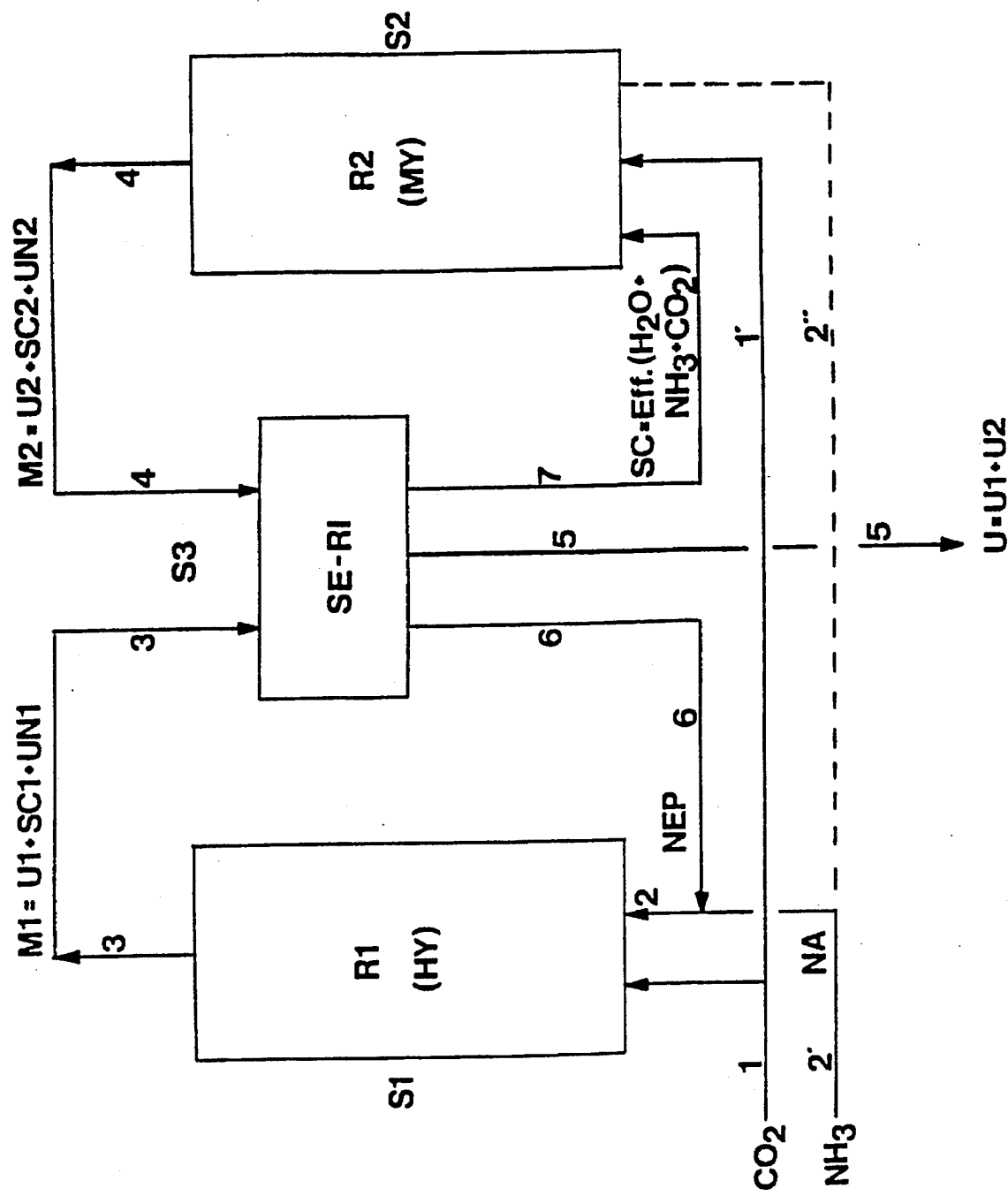
FIG. 2 is a diagrammatic representation of the process of this invnetion.

The different aspects and advantages of the invention are seen better in the description of its preferred embodiment illustrated in scheme of FIG. 2.

In FIG. 2 is represented a form of simple and efficacious and therefore advantageous embodiment of the process according to the invention in its more significant conceptual features.

These derive from the fact that the process can be represented schematically as essentially constituting of three sections, two of reaction S1 and S2 of differentiated yield and the last one of recycling SE-RI (S3). S1 includes the reactor R1 fed, characteristically, only (or substantially only) with pure reactants CO2 (line 1) and NH3 (line 2). Receiving only reactants of high purity, R1 is to be considered immediately as reactor of high yield (HY).

The mixture M1 of the reaction products in R1 (HY), made up substantially of urea U1, of the carbamate solution SC1 and the unreacted compounds UN1 (principally NH3 fed in excess from line 2'), is brought from line 3 to recycling section SE-RI, to which is made flow into, through line 4, the same mixture M2 of the products from the reaction in the second reactor R2, mixture made up of urea U2, of carbamate solution SC2 and of unreacted compounds UN2 (principally NH3 fed in excess). From the said recycling section (SE-RI, outflow: 1) on line 5, all the produced urea (U) resulting from the partial ones (U1) and (U2) obtained in the two respective reactors R1 and R2; 2) on line 6, ammonia of high purity NEP which, according to a feature of the invention, is recycled again only into reactor R1 together with NH3 fed from the outside (line 2'), having NEP (6) purity substantially compatible with the last one (NA); c) one line 7, the aqueous effluent SC=Eff. (H2O+NH3+CO2), i.e. the mixture consisting in the carbamate aqueous solution and NH3 in excess.

Characteristically, the last aqueous effluent (SC) rich in NH3 of low purity grade and contains CO2, is recycled, through line 7, only into reactor R2 which, receiving reactants less pure than the ones fed into R1, has an average yield (MY), i.e. inferior to the one of R1 (HY).

R2 received fresh CO2 from feeding 1 on line 1' and eventually additional quantity of fresh NH3 on line 2".

The applications of the process, according to the invention, to the conventional systems with separate recycling of NH3 in order to improve substantially the performances are of particular importance.

Figure 3:
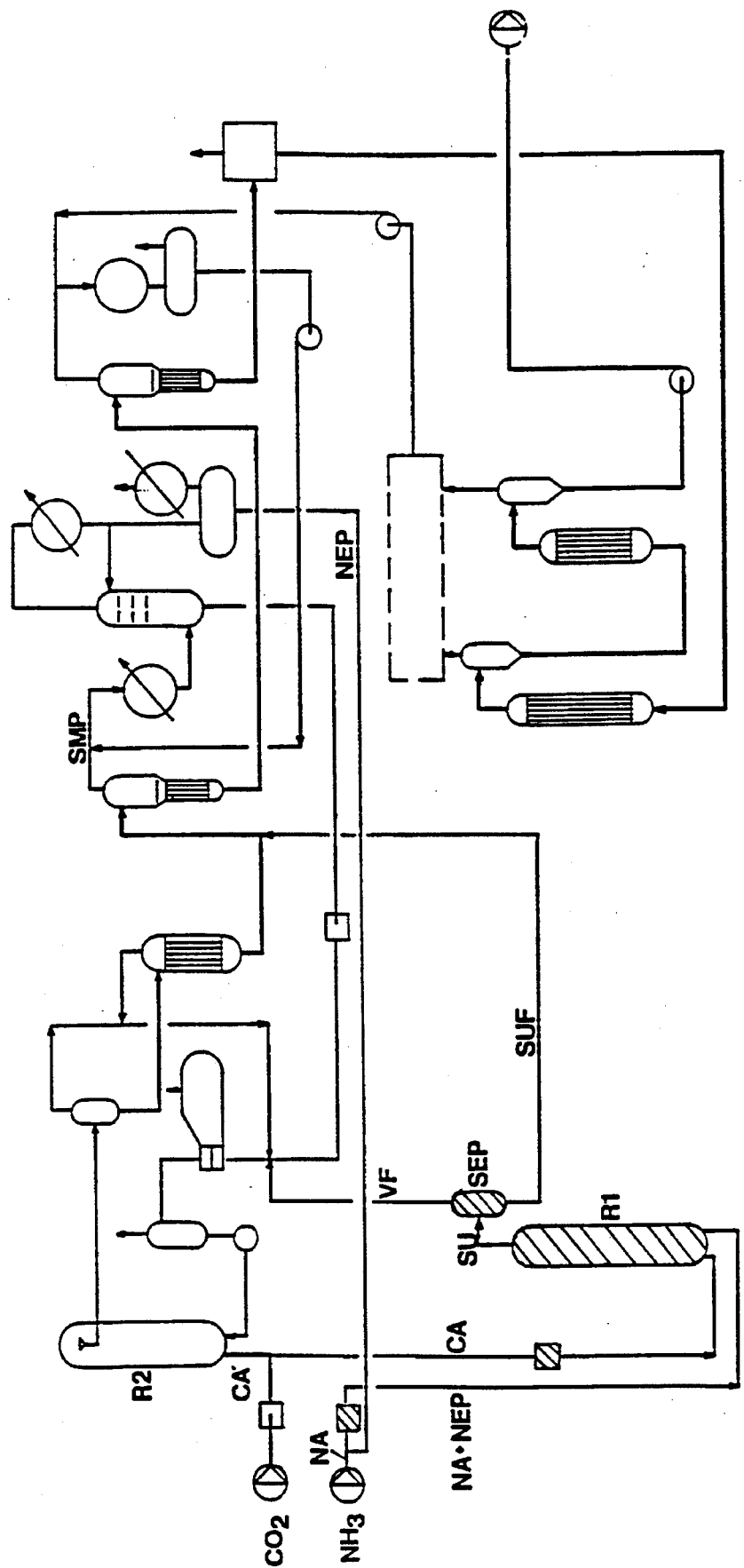
FIG. 3 diagrammatically illustrates the process of this invention applied to the prior art Snamprogetti process.

As a not limitative example, we describe in FIG. 3 the application to the selfstripping process NH3 of Snamprogetti.

Such a process, as most of the urea processes used actually on industrial scale, is of total recycling type, which means that unreacted NH3 and CO2 coming out of the reactor (or out of isobaric stripper) and recycled to the reactor in form of aqueous solution. The presence of recycled H2O in the reactor reduces the yield of carbamate conversion into urea penalizing the capacity and the consumption of the plant.

On the other side, it is known that feeding a synthesis reactor with only pure reactants (NH3 and CO2) we can obtain very high yields. For example in the process known as "Vulcan" (now abandoned) the following results are reached:

NH3/CO2 in the reactor: 4.5
H2O/CO2 in the reactor: 0
P: 400 bar
T: 215° C.
yield: 80%
Volume of reactor: 0.05 m3/td urea To be noted that above mentioned values have been reached (and still can be reached) for years on industrial scale in synthesis reactor lined with zirconium, against corrosion. This system has been abandoned because the recovery of residual reactants not transformed in the reactor was complex and uneconomical, by means of a selective chemical separation in order to obtain NH3 of high purity to recycle into the reactor.

According to the present invention (see FIG. 3), the excess of separated ammonia (NEP) in the recycling sections of the Snamprogetti process (or in processes Toyo TRC and TRC-I), together with fresh feeding ammonia (NA), is fed (NA+NEP) into the reactor (R1) of very high yield "once through" for example of the "Vulcan" type operating with pressures above 300 bar and temperature above 190 ° C., where it is transformed into urea together with part of the fresh CO2 (CA) fed in the stoichiometric quantity requested for reaching the desired ratio NH3/CO2 higher than 4, having now the conventional reactor (R2) foreseen in the Snamprogetti scheme (and operating with pressure lower than 300 bar and at temperature lower or equal to 190 ° C.), the function of transforming into urea the only carbamate recycle (SC) together with the remaining part of fresh CO2 (CA') fed into said reactor in such quantity as to maintain in it ratios NH3/CO2 lower 4.

In a preferred embodiment form, the new plant for obtaining the transformation of reactants into urea with very high yields includes two reactors in parallel, the first of which works as "one through" (without recycles) at high pressure (from 250 to 450 bar) and temperatures between 200°–220° C., fed substantially with ammonia and pure CO2, and the second reactor working at lower pressure, for example 130–200 bar and lower temperatures, for example 180°–200° C. (better if lower than 190° C.) coupled with a total recycle system and consequently, functioning with feeding of part of the fresh reactants not sent into the first reactor and recuperating all the recycle of the total recycle system.

In particular, the solution of urea (SU) coming out of the reactor (R1) is preferably expanded in the separator (SEP) operating at reactor pressure (R2) and the freed flash vapours (VF) are sent into the reactor (R2) whilst the solution of flash urea (SUF) is sent into the section at medium pressure (SMP) for the recovery of the unreacted substances (NH3 and CO2).

With this system, in the above mentioned reactors (R1 respectively R2) yields of transformation into urea are reached, in the first one superior from 75 to 85% and in the second one from 60 to 70%; therefore the yield of combined transformation of the synthesis system is very high depending from the optimal distribution of load between the two reactors.

As already anticipated, the advantage of the process according to the invention is that it can be conveniently used for the realization of new production plants of high yields and low energy consumptions as well as for the improvement of urea processes with separate recycle of NH3 for example of Snamprogetti type (FIG. 3) or Toyo Engineering Ltd.

As already mentioned, a plant modernized by the application of the invention to conventional systems is characterized by the addition of one reactor of high yield R1 and of the devices for bringing the reactants to the higher operative conditions of R1 compared with the old reactor R2.

A new plant is obtained simply by the implementation of the process scheme according to FIG. 2.

EXAMPLE 1

An example referred to the Snamprogatti process (see scheme of FIG. 3) is given hereunder: the recycle NH3 of high purity (NEP) which is pumped into the reactor is 0.4 (*) times the stoichiometry feeding NH3 (Nλ).

(*) to be noted that in the Snamprogetti plants the recycle NH3 of high purity can variate from 0.3 to 0.5 times the feeding and more, whilst in the following example, absolutely not limitative of the invention, an average value of 0.4 has been presumed.

Feeding with total NH3 (Nλ+NEP) the parallel reactor R1 (high efficiency parallel converter HY) type "once through" proposed by the present invention, we have:

available NH3: ≈1.4×570=798 kg/t urea=46.94 kmol/t urea

NH3CO2: 4.5 mol necessary CO2: $^{46.94}/_{4.5}$=10.43 Kmol/t=459 kg/t

H2O/CO2: 0

With an obtainable yield of 80%, the CO2 transformed into urea is:

$$459 \times 0.8 = 367.2 \text{ kg/t} = 367.2 \frac{60}{44} = \approx 500 \text{ kg urea/t urea}$$

It is therefore possible to produce approx. 50% of the urea in reactor R1, i.e. in high yield conditions.

A Snamprogetti plant with reactor in parallel of high yield (HY) will therefore operate with an average yield equal to approx.

$$\frac{63 + 80}{2} = 71.5\%$$

and the vapour consumptions will consequently be notably reduced (550–600 kg/t urea against the conventional value of 900 kg/t).

The invention is susceptible to all these variants and modifications which for being within each reach of a skilled person, have to be considered as falling within the scope and spirit of this invention.

It can be worth mentioning that in the U.S. Pat. No. 4,670,588 a process with two reaction zones or reactors in series is described, the philosophy of which is however completely different from the one of the present invention.

Also in the "IDR" it is possible to utilize reactors with two isobaric zones in series functioning with diverse molar ratios of the reactants.

I claim:

1. A method of retrofitting a pre-existing plant for urea production including:

a first urea synthesis reactor;

means for feeding high purity ammonia and carbon dioxide to said first reactor;

a carbamate condenser downstream of said first urea synthesis reactor;

an isobaric stripper downstream of said first urea synthesis reactor;

a recovery section for separating urea produced in the first urea synthesis reactor from an aqueous solution of unreacted products, said recovery section comprising:
 a medium pressure section downstream of said isobaric stripper, for distilling an urea solution produced in the first urea synthesis reactor;
 a rectification column, downstream of said medium pressure section, for separating high purity ammonia and said aqueous solution of unreacted products out of a vapor stream leaving said medium pressure section;

conduit means for recycling said aqueous solution of unreacted products leaving the rectification column to said carbamate condenser;

conduit means for recycling said high purity ammonia leaving the rectification column to said first urea synthesis reactor;

said method comprising the steps of:
 a) providing a second urea synthesis reactor upstream of said recovery section;
 b) disconnecting said means for feeding high purity ammonia and said conduit means for recycling said high purity ammonia leaving the rectification column from the first urea synthesis reactor and connecting the same to the second urea synthesis reactor;
 c) connecting means for feeding high purity carbon dioxide to said second reactor;
 d) providing a flash separator downstream of said second urea synthesis reactor;
 e) providing conduit means for feeding to said carbamate condenser a vapor stream leaving said flash separator;
 f) providing conduit means for feeding to said medium pressure section a urea stream leaving said flash separator.

2. A method according to claim 1, characterized in that said first urea synthesis reactor is of the "once through" high-yield type operating at a pressure of from 250 to 450 bar and at a temperature of from 200° to 220° C.

3. A method according to claim 1, characterized in that said second urea synthesis reactor operates at a pressure of from 130 to 200 bar and at a temperature of from 180° to 200° C.

* * * * *